(12) United States Patent
Erbs (10) Patent No.: US 8,470,591 B2
(45) Date of Patent: Jun. 25, 2013

(54) KIT OF PARTS DESIGNED FOR IMPLEMENTING AN ANTITUMORAL OR ANTIVIRAL TREATMENT IN A MAMMAL

(75) Inventor: Philippe Erbs, Strasbourg (FR)

(73) Assignee: Transgene S.A., Illkirch (FR)

( * ) Notice: Subject to any disclaimer, the term of this patent is extended or adjusted under 35 U.S.C. 154(b) by 363 days.

(21) Appl. No.: 11/667,254

(22) PCT Filed: Oct. 26, 2005

(86) PCT No.: PCT/IB2005/003435
§ 371 (c)(1),
(2), (4) Date: May 8, 2007

(87) PCT Pub. No.: WO2006/048768
PCT Pub. Date: May 11, 2006

(65) Prior Publication Data
US 2009/0170795 A1 Jul. 2, 2009

Related U.S. Application Data

(60) Provisional application No. 60/646,595, filed on Jan. 26, 2005.

(30) Foreign Application Priority Data

Nov. 8, 2004 (EP) .................................... 04360101

(51) Int. Cl.
| | |
|---|---|
| C12N 15/00 | (2006.01) |
| C12N 15/09 | (2006.01) |
| A01N 63/00 | (2006.01) |
| C07H 21/02 | (2006.01) |
| C07H 21/04 | (2006.01) |

(52) U.S. Cl.
USPC ..... 435/320.1; 424/93.2; 536/23.1; 536/23.2; 536/23.4; 536/23.7

(58) Field of Classification Search
USPC ............. 424/93.2; 435/320.1; 536/23.1, 23.2, 536/23.4, 23.7
See application file for complete search history.

(56) References Cited

U.S. PATENT DOCUMENTS

| | | | | |
|---|---|---|---|---|
| 5,856,153 | A * | 1/1999 | Tiraby et al. | 435/455 |
| 5,858,707 | A * | 1/1999 | Guimaraes et al. | 435/69.1 |
| 6,153,740 | A * | 11/2000 | Young et al. | 536/23.5 |
| 6,552,005 | B1 * | 4/2003 | Buchsbaum et al. | 514/44 R |
| 6,596,533 | B1 * | 7/2003 | Erbs et al. | 435/320.1 |
| 6,749,863 | B1 * | 6/2004 | Chang et al. | 424/450 |

OTHER PUBLICATIONS

Balloul et al., 2003, US 20030165477 A1.*
Brethes et al., 1992, Eur. J. Biochem., vol. 204, p. 699-704.*
Gupta et al., 1995, FEMS Microbiology Letters, vol. 126, p. 93-96.*
Koike et al., "A Canalicular Multispecific Organic Anion Transporter (cMOAT) Antisense cDNA Enhances Drug Sensitivity in Human Hepatic Cancer Cells[1] ", Cancer Research, vol. 57, pp. 5475-5479, Dec. 15, 1997, The American Association for Cancer Research, Baltimore, MD, US.
Patel et al., "Retroviral transfer of the hENT2 nucleoside transporter cDNA confers broad-spectrum antifolate resistance in murine bone marrow cells", Blood, vol. 95, No. 7, pp. 2356-2363, Apr. 1, 2000, The American Society of Hermatology, US.
Anand et al., "Current prodrug strategies via membrane transporters/receptors", Expert Opin. Biol. Ther., vol. 2, No. 6, Aug. 2002, pp. 607-620, Ashley Publications, Ltd., Great Britain.
Damaraju et al., "Nucleoside anticancer drugs: the role of nucleoside transporters in resistance to cancer chemotherapy", Oncogene, vol. 22, pp. 7524-7536, Oct. 20, 2003, Nature Publishing Group.
G.A. Chung-Faye et al., *In vivo gene therapy for colon cancer using adenovirus-mediated, transfer of the fusion gene cytosine deaminase and uracil phosphoribosyltransferase*, 8 Gene Therapy 1547-1554 (2001).
P. Erbs et al., *In Vivo Cancer Gene Therapy by Adenovirus-mediated Transfer of a Bifunctional Yeast Cytosine Deaminase/Uracil Phosphoribosyltransferase Fusion Gene*, 60 Cancer Research 3813-3822 (Jul. 15, 2000).
F. Koyama et al., *Combined suicide gene therapy for human colon cancer cells using adenovirus-mediated transfer of Escherichia coli cytosine deaminase gene and Escherichia coli uracil phosphoribosyltransferase gene with 5-fluorocytosine*, 7(7) Cancer Gene Therapy 1015-1022 (2000).
M. Tiraby et al., *Concomitant expression of E. coli cytosine deaminase and uracil phosphoribosyltransferase improves the cytotoxicity of 5-fluorocytosine*, 167 FEMS Microbiology Letters 41-49 (1998).
E. Weber et al., *The purine-cytosine permease gene of Saccharomyces cerevisiae: primary structure and deduced protein sequence of the FCY2 gene product*, 4(4) Molecular Microbiology 585-596 (1990).
Partial English language translation of a Japanese Official Action mailed Feb. 15, 2011, issued in corresponding Japanese Patent Application No. 2007-539650.
I. Hapala et al., *Effect of ergosterol on the activity of purine-cytosine permease in the yeast Saccharomyces cerevisiae*, 52(Focus Issue) Chem Papers 410 (1998).
M. Opekarova et al., *Specific lipid requirements of membrane proteins—a putative bottleneck in heterologous expression*, 1610 Science 11-22 (2003).
Ergosterol from Wikipedia, http://en.wikipedia.org/wiki/Ergosterol printed on Sep. 28, 2012.

* cited by examiner

*Primary Examiner* — Shin-Lin Chen
(74) *Attorney, Agent, or Firm* — Buchanan Ingersoll & Rooney PC (57) ABSTRACT

The present invention relates to a kit of parts comprising a nucleic acid sequence encoding a permease and a drug comprising one nucleobase moiety or a precursor thereof. The present invention further relates to a kit of parts comprising a precursor of a drug comprising a gene coding a permease and a nucleic acid sequence comprising a suicide gene. The present invention also relates to a vector comprising a gene coding a permease and a suicide gene.

18 Claims, 3 Drawing Sheets

SEQUENCE LISTING

<160> NUMBER OF SEQ ID NOS: 4

<210> SEQ ID NO 1
<211> LENGTH: 533
<212> TYPE: PRT
<213> ORGANISM: Saccharomyces cerevisiae

<400> SEQUENCE: 1

```
Met Val Glu Glu Gly Asn Asn Val Tyr Glu Ile Gln Asp Leu Glu Lys
 1               5                  10                  15

Arg Ser Pro Val Ile Gly Ser Ser Leu Glu Asn Glu Lys Lys Val Ala
             20                  25                  30

Ala Ser Glu Thr Phe Thr Ala Thr Ser Glu Asp Asp Gln Gln Tyr Ile
         35                  40                  45

Val Glu Ser Ser Glu Ala Thr Lys Leu Ser Trp Phe His Lys Phe Phe
     50                  55                  60

Ala Ser Leu Asn Ala Glu Thr Lys Gly Val Glu Pro Val Thr Glu Asp
 65                  70                  75                  80

Glu Lys Thr Asp Asp Ser Ile Leu Asn Ala Ala Ser Met Trp Phe Ser
             85                  90                  95

Ala Asn Met Val Ile Ala Ser Tyr Ala Leu Gly Ala Leu Gly Pro Met
            100                 105                 110

Val Phe Gly Leu Asn Phe Gly Gln Ser Val Leu Val Ile Ile Phe Phe
        115                 120                 125

Asn Ile Met Gly Leu Ile Phe Val Ala Phe Phe Ser Val Phe Gly Ala
130                 135                 140

Glu Leu Gly Leu Arg Gln Met Ile Leu Ser Arg Tyr Leu Val Gly Asn
145                 150                 155                 160

Val Thr Ala Arg Ile Phe Ser Leu Ile Asn Val Ile Ala Cys Val Gly
                165                 170                 175

Trp Gly Ile Val Asn Thr Ser Val Ser Ala Gln Leu Leu Asn Met Met
            180                 185                 190

Asn Glu Gly Ser Gly His Val Cys Pro Ile Trp Ala Gly Cys Leu Ile
        195                 200                 205

Ile Ile Gly Gly Thr Val Leu Val Thr Phe Phe Gly Tyr Ser Val Ile
    210                 215                 220

His Ala Tyr Glu Lys Trp Ser Trp Val Pro Asn Phe Ala Val Phe Leu
225                 230                 235                 240

Val Ile Ile Ala Gln Leu Ser Arg Ser Gly Lys Phe Lys Gly Gly Glu
                245                 250                 255

Trp Val Gly Gly Ala Thr Thr Ala Gly Ser Val Leu Ser Phe Gly Ser
            260                 265                 270

Ser Ile Phe Gly Phe Ala Ala Gly Trp Thr Thr Tyr Ala Ala Asp Tyr
        275                 280                 285

Thr Val Tyr Met Pro Lys Ser Thr Asn Lys Tyr Lys Ile Phe Phe Ser
    290                 295                 300

Leu Val Ala Gly Leu Ala Phe Pro Leu Phe Phe Thr Met Ile Leu Gly
305                 310                 315                 320

Ala Ala Ser Ala Met Ala Ala Leu Asn Asp Pro Thr Trp Lys Ala Tyr
                325                 330                 335

Tyr Asp Lys Asn Ala Met Gly Gly Val Ile Tyr Ala Ile Leu Val Pro
            340                 345                 350

Asn Ser Leu Asn Gly Phe Gly Gln Phe Cys Cys Val Leu Leu Ala Leu
        355                 360                 365
```

```
Ser Thr Ile Ala Asn Asn Ile Pro Asn Met Tyr Thr Val Ala Leu Ser
    370                 375                 380

Ala Gln Ala Leu Trp Ala Pro Leu Ala Lys Ile Pro Arg Val Val Trp
385                 390                 395                 400

Thr Met Ala Gly Asn Ala Ala Thr Leu Gly Ile Ser Ile Pro Ala Thr
                405                 410                 415

Tyr Tyr Phe Asp Gly Phe Met Glu Asn Phe Met Asp Ser Ile Gly Tyr
            420                 425                 430

Tyr Leu Ala Ile Tyr Ile Ala Ile Ser Cys Ser Glu His Phe Phe Tyr
        435                 440                 445

Arg Arg Ser Phe Ser Ala Tyr Asn Ile Asp Asp Trp Asp Asn Trp Glu
    450                 455                 460

His Leu Pro Ile Gly Ile Ala Gly Thr Ala Ala Leu Ile Val Gly Ala
465                 470                 475                 480

Phe Gly Val Ala Leu Gly Met Cys Gln Thr Tyr Trp Val Gly Glu Ile
                485                 490                 495

Gly Arg Leu Ile Gly Lys Tyr Gly Gly Asp Ile Gly Phe Glu Leu Gly
            500                 505                 510

Ala Ser Trp Ala Phe Ile Ile Tyr Asn Ile Leu Arg Pro Leu Glu Leu
        515                 520                 525

Lys Tyr Phe Gly Arg
    530

<210> SEQ ID NO 2
<211> LENGTH: 633
<212> TYPE: PRT
<213> ORGANISM: Saccharomyces cerevisiae

<400> SEQUENCE: 2

Met Ala Asp Asn Leu Ser Leu His Leu Ser Gly Ser Ser Lys Arg Leu
1               5                   10                  15

Asn Ser Arg Gln Leu Met Glu Ser Ser Asn Glu Thr Phe Ala Pro Asn
            20                  25                  30

Asn Val Asp Leu Glu Lys Glu Tyr Lys Ser Ser Gln Ser Asn Ile Thr
        35                  40                  45

Thr Glu Val Tyr Glu Ala Ser Ser Phe Glu Glu Lys Val Ser Ser Glu
    50                  55                  60

Lys Pro Gln Tyr Ser Ser Phe Trp Lys Lys Ile Tyr Tyr Glu Tyr Val
65                  70                  75                  80

Val Val Asp Lys Ser Ile Leu Gly Val Ser Ile Leu Asp Ser Phe Met
                85                  90                  95

Tyr Asn Gln Asp Leu Lys Pro Val Glu Lys Glu Arg Arg Val Trp Ser
            100                 105                 110

Trp Tyr Asn Tyr Cys Tyr Phe Trp Leu Ala Glu Cys Phe Asn Ile Asn
        115                 120                 125

Thr Trp Gln Ile Ala Ala Thr Gly Leu Gln Leu Gly Leu Asn Trp Trp
    130                 135                 140

Gln Cys Trp Ile Thr Ile Trp Ile Gly Tyr Gly Phe Val Gly Ala Phe
145                 150                 155                 160

Val Val Leu Ala Ser Arg Val Gly Ser Ala Tyr His Leu Ser Phe Pro
                165                 170                 175

Ile Ser Ser Arg Ala Ser Phe Gly Ile Phe Phe Ser Leu Trp Pro Val
            180                 185                 190

Ile Asn Arg Val Val Met Ala Ile Val Trp Tyr Ser Val Gln Ala Tyr
        195                 200                 205
```

```
Ile Ala Ala Thr Pro Val Ser Leu Met Leu Lys Ser Ile Phe Gly Lys
    210                 215                 220
Asp Leu Gln Asp Arg Ile Pro Asp His Phe Gly Ser Pro Asn Ala Thr
225                 230                 235                 240
Thr Tyr Glu Phe Met Cys Phe Phe Ile Phe Trp Ala Ala Ser Leu Pro
                    245                 250                 255
Phe Leu Leu Val Pro Pro His Lys Ile Arg His Leu Phe Thr Val Lys
                260                 265                 270
Ala Val Leu Val Pro Phe Ala Ser Phe Gly Phe Leu Ile Trp Ala Ile
            275                 280                 285
Arg Arg Ala His Gly Arg Ile Ala Leu Gly Ser Leu Thr Asp Val Gln
        290                 295                 300
Pro His Gly Ser Ala Phe Ser Trp Ala Phe Leu Arg Ser Leu Met Gly
305                 310                 315                 320
Cys Met Ala Asn Phe Ser Thr Met Val Ile Asn Ala Pro Asp Phe Ser
                    325                 330                 335
Arg Phe Ser Lys Asn Pro Asn Ser Ala Leu Trp Ser Gln Leu Val Cys
                340                 345                 350
Ile Pro Phe Leu Phe Ser Ile Thr Cys Leu Ile Gly Ile Leu Val Thr
            355                 360                 365
Ala Ala Gly Tyr Glu Ile Tyr Gly Ile Asn Tyr Trp Ser Pro Leu Asp
        370                 375                 380
Val Leu Glu Lys Phe Leu Gln Thr Thr Tyr Asn Lys Gly Thr Arg Ala
385                 390                 395                 400
Gly Val Phe Leu Ile Ser Phe Val Phe Ala Val Ala Gln Leu Gly Thr
                    405                 410                 415
Asn Ile Ser Ala Asn Ser Leu Ser Cys Gly Thr Asp Met Ser Ala Ile
                420                 425                 430
Phe Pro Lys Phe Ile Asn Ile Lys Arg Gly Ser Leu Phe Cys Ala Ala
            435                 440                 445
Met Ala Leu Cys Ile Cys Pro Trp Asn Leu Met Ala Thr Ser Ser Lys
        450                 455                 460
Phe Thr Met Ala Leu Ser Ala Tyr Ala Ile Phe Leu Ser Ser Ile Ala
465                 470                 475                 480
Gly Val Val Cys Ser Asp Tyr Phe Val Val Arg Arg Gly Tyr Ile Lys
                    485                 490                 495
Leu Thr His Ile Tyr Ser His Gln Lys Gly Ser Phe Tyr Met Tyr Gly
                500                 505                 510
Asn Arg Phe Gly Ile Asn Trp Arg Ala Leu Ala Ala Tyr Leu Cys Gly
            515                 520                 525
Val Ala Pro Cys Leu Pro Gly Phe Ile Ala Glu Val Gly Ala Pro Ala
        530                 535                 540
Ile Lys Val Ser Asp Gly Ala Met Lys Leu Tyr Tyr Leu Ser Tyr Trp
545                 550                 555                 560
Val Gly Tyr Gly Leu Ser Phe Ser Ser Tyr Thr Ala Leu Cys Tyr Phe
                    565                 570                 575
Phe Pro Val Pro Gly Cys Pro Val Asn Asn Ile Ile Lys Asp Lys Gly
                580                 585                 590
Trp Phe Gln Arg Trp Ala Asn Val Asp Phe Glu Glu Glu Trp Lys
            595                 600                 605
Asp Thr Ile Glu Arg Asp Asp Leu Val Asp Asp Asn Ile Ser Val Tyr
        610                 615                 620
Glu His Glu His Glu Lys Thr Phe Ile
```

-continued

```
<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
taacgatctc gagccatggt ggaagaggga aataatgttt acg                            43

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccctaatcac gcgttcctaa cgaccgaagt attttaat                                  38
```

KIT OF PARTS DESIGNED FOR IMPLEMENTING AN ANTITUMORAL OR ANTIVIRAL TREATMENT IN A MAMMAL

This application is the United States national phase of International Application No. PCT/IB2005/003435, filed Oct. 26, 2005, published in English as International Publication No. WO 2006/048768 on May 11, 2006, which claims benefit of U.S. Provisional Application No. 60/646,595, filed Jan. 26, 2005, and claims priority of Application No. 04360101.2 filed in the European Patent Office on Nov. 8, 2004, the earlier applications being incorporated by reference herein in their entireties and relied upon.

The present invention relates to a kit of parts comprising a nucleic acid sequence encoding a permease and a drug comprising one nucleobase moiety or a precursor thereof. The present invention further relates to a kit of parts comprising a precursor of a drug comprising one nucleobase moiety, a nucleic acid sequence comprising a gene coding a permease and a nucleic acid sequence comprising a suicide gene. The present invention also relates to a vector comprising a gene coding a permease and a suicide gene. The present invention is particularly useful in the context of carrying out a gene therapy treatment of proliferative or infectious diseases.

Drugs comprising one nucleobase moiety are the most widely used drugs for the treatment of cancer or viral infection. Among them nucleoside analogues such as cytarabine, gemcitabine, fludarabine, cladribine, troxacitabine and clofarabine are currently used in cancer chemotherapy. Nucleoside analogues are antimetabolites which interfere with nucleic acid synthesis. These agents are generally S-phase specific, and can exert cytotoxic activity either by being incorporated and altering the DNA and RNA macromolecules themselves, and/or by interfering with various enzymes involved in nucleic acid synthesis, and/or by modifying the metabolism of physiologic nucleosides.

Nucleoside analogues were also among the first compounds shown to be effective against viral infections. For example, the first four anti-HIV drugs to be approved, AZT, ddI, ddC and D4T; were nucleoside analogues. All four of these drugs and other nucleoside analogues are believed to have a similar mechanism of HIV inhibition, in which the nucleosides are progressively phosphorylated to a 5'-triphosphate, which then acts as a chain terminator in a reverse transcriptase (RT) reaction.

Nucleobase analogues are also used in the treatment of cancer. For example fluorouracil (5-FU) is a fluorinated pyrimidine that is metabolized intracellulary to its active form, fluorodeoxyuridine monophophate (FdUMP). The active form inhibits DNA synthesis by inhibiting the normal production of thymidine. Fluorouracil is given intravenously to treat colon, rectum, breast, stomach, and pancreas cancers. Fluorouracil is also available in creams and solutions for topical treatment of some skin cancers and genital warts.

The development of gene therapy has opened new possibilities for the use of drug comprising one nucleobase moiety. This particular domain of gene therapy which is called "suicide gene therapy" uses genes whose expression products are able to transform an inactive substance (a prodrug) into a cytotoxic substance, thereby giving rise to cell death.

The gene encoding the herpes simplex type I virus thymidine kinase (HSV-1 TK) constitutes the prototype of the suicide genes (Caruso et al., 1993, Proc. Natl. Acad. Sci. USA 90, 7024-7028; Culver et al., 1992, Science 256, 1550-1552; Ram et al., 1997, Nat. Med. 3, 1354-1361). While the TK polypeptide is not toxic as such, it catalyzes the transformation of nucleoside analogues such as acyclovir or ganciclovir (GCV). The modified nucleosides are incorporated into the DNA chains which are in the process of elongation, inhibiting cell division as a consequence. A large number of suicide gene/prodrug pairs are currently available. Those which may more specifically be mentioned *Escherichia coli* (*E. Coli*) purine nucleoside phosphorylase and 6-methylpurine deoxyribonucleoside (Sorscher et al., 1994, Gene Therapy 1, 223-238), *E. coli* guanine phosphoribosyl transferase and 6-thioxanthine (Mzoz and Moolten, 1993, Human Gene Therapy 4, 589-595) and cytosine deaminase (CDase) and 5-fluorocytosine (5FC).

In human, the transport of drugs comprising one nucleobase moiety across the cell membrane is passive or made by dedicated membraneous transporter. For example, most of the nucleoside analogues are hydrophilic molecules and their transport through the cell membrane is regulated by membrane transporter. In mammalian cells, there are two major nucleoside transporter gene families: the equilibrative nucleoside transporters (ENTs) and the concentrative nucleoside transporters (CNTs). The ENTs are facilitated carrier proteins and the CNTs are Na(+)-dependent secondary active transporters (Kong et al., 2004, Curr Drug Metab, 5:63-84) The nucleoside transporters are implicated in resistance to anticancer nucleoside analogues. A single nucleotide polymorphisms (SNPs) in drug transporters may contribute to interindividual variation in response to nucleoside analogues (Damaraju et al., Oncogene. 2003, 22: 7524-36). Therefore, there is need for a new therapeutic strategy which can circumvent a low or non-existent expression of the nucleoside transporters. Moreover, there is also a need to enhance the intracellular concentration of drugs comprising one nucleobase moiety as the intracellular concentration is correlated with the therapeutic efficiency.

One of the goals of the present invention is to improve the intracellular concentration of drugs comprising one nucleobase moiety into cells (e.g. tumoral cells or virally infected cells). This goal is achieved by the transfection of the target cells by a nucleic acid sequence comprising a gene coding a permease.

The present invention also aims to improve the efficacy of suicide gene therapy, by using in combination a nucleic acid sequence comprising a gene coding a permease and a nucleic acid sequence comprising a suicide gene. This particular use improves the intracellular concentration of the prodrug (i.e. the precursor of a drug comprising a nucleobase moiety) which can be converted by the protein encoded by the suicide gene. This use may also improve the bystander effect by enhancing the transfer of the drug from the cells transfected by the suicide gene to the cells expressing the permease.

With this respect, the present invention also allows to use lower amount of drugs or prodrugs and to reduce the side effects induced by such treatments.

For this purpose, the present invention provides a kit of parts comprising:
- a drug comprising one nucleobase moiety or a precursor thereof, and
- a nucleic acid sequence comprising a gene coding a permease.

According to another embodiment, the present invention also provides a kit of parts comprising:
- a precursor of a drug comprising one nucleobase moiety, and
- a nucleic acid sequence comprising a gene coding a permease, and
- a nucleic acid sequence comprising a suicide gene.

In a preferred embodiment, the kit of parts according to the invention is intended to be used for the treatment of cancer and/or viral diseases in vertebrates and more particularly in humans.

As used herein a drug comprising one nucleobase moiety is a molecule which comprise in its structure only one nucleobase moiety. According to a preferred embodiment of the invention, the drug comprising one nucleobase moiety is able to kill cells and more preferably to kill tumoral cells. According to another preferred embodiment, the drug comprising one nucleobase moiety is able to reduce or prevent the replication of a virus in a cell.

According to the invention a nucleobase moiety is chosen from the group consisting in Adenine, Thymine, Guanine, Uracil, Cytosine and analogues thereof.

According to a preferred embodiment of the invention, a drug comprising one nucleobase moiety is chosen from the group comprising
- nucleoside analogues such as cytarabine, gemcitabine, capecitabine, fludarcibine, cladribine, troxacitabine, clofarabine, azidothymidine (AZT), didanosine (ddI), zalcitabine (ddC), stavudine (d4T), fluoromethylene deoxycytidine (FMdC) and lamivudine, floxuridine (FUdR) and
- Pyrimidine analogues such as 5-fluorouracil (5-FU), and
- Purine analogues such as thioguanine, mercaptopurine, acyclovir, valacyclovir, famcyclovir, ganciclovir.

As used herein, a precursor of a drug comprising one nucleobase moiety refers to a molecule which can be converted by one or more enzymatic reaction into a drug comprising one nucleobase moiety.

According to a preferred embodiment of the invention, a precursor of a drug comprising one nucleobase moiety is chosen from the group comprising azidothymidine (AZT), Gancyclovir (GCV), 5-Fluorocytosine (5-FC), 5-Fluorouracil (5-FU), 6-Methylpurine deoxyribonucleoside, Ganciclovir elaidic acid ester, penciclovir, Acyclovir, Valacyclovir, (E)-5-(2-bromovinyl)-2'-deoxyuridine,zidovudine, 2'-Exomethanocarbathymidine.

As used herein, permease refers to transmembraneous protein involved in the transfer of a drug comprising one nucleobase moiety, or a precursor thereof through the cell membrane.

The permease according to the invention notably refers to purine permease, cytosine permease and nucleoside transporters.

According to a preferred embodiment of the invention, permease is a purine or a cytosine permease of S. Cerevisiae. The nucleobase transporters of S. cerevisiae consist of the purine-cytosine permease, known as FCY2, and the uracil permease, known as FUR4. According to a more preferred embodiment of the invention, the permease has an amino acid sequence chosen from the group comprising SEQ ID NO:1 and SEQ ID NO:2.

The purine-cytosine permease, FCY2 mediates symport of protons and adenine, guanine, hypoxanthine and cytosine across the yeast plasma membrane (Grenson 1969, Jund and Lacroute 1970, Polak and Grenson 1973, Chevallier et al. 1975, Hopkins et al. 1988). FCY2 protein mediates also the transport of 5-fluorocytosine, an analogue of cytosine (Grenson 1969, Jund and Lacroute 1970). FCY2 gene encodes a protein of 533 amino acids (58 kDa) initially predicted to have 10-12 transmembrane-spanning domains (Weber et al. 1990), with nine now favoured (Ferreira et al. 1999). FCY2 exhibits similar affinities for the purine nucleobases and cytosine (Brethes et al. 1992). Uracil uptake into S. cerevisiae is mediated by the uracil permease, FUR4 (Jund and Lacroute 1970, Jund et al. 1977). FUR4 is a uracil-proton symporter (Hopkins et al. 1988) predicted to be a protein of 633 amino acids (71.7 kDa) with 10 transmembrane domains and long cytoplasmic hydrophylic N- and C-terminal tails (Jund et al. 1988, Garnier et al. 1996). FUR4 protein can also mediates the transport of 5-fluorouracil, an analogue of uracil (Jund and Lacroute 1970).

With this respect, according to a preferred embodiment, the permease is chosen from the group comprising FCY2 and Fur4 and analogues thereof. Amino acid sequences of FCY2 and Fur4 are notably available in the swissprot database (accession number P17064 and P05316 respectively). Analogues of Fur4 and FCY2 refers to polypeptide having an amino acid sequence which have at least a degree of identity greater than 70%, advantageously greater than 80%, preferably greater than 90%, and most preferably greater than 95% with the amino acid sequence of the parent protein and which retains the ability to transport a drug comprising one nucleobase moiety through the cell membrane According to another preferred embodiment, the permease is chosen from the group comprising hENT1, hENT2, hCNT1, hCNT2 and hCNT3 and analogues thereof. The amino acid sequences of these permeases are available to the one skilled in the art, notably in the swissprot database. Analogues of these polypeptides refers to a polypeptide having an amino acid sequence which have at least a degree of identity greater than 70%, advantageously greater than 80%, preferably greater than 90%, and most preferably greater than 95% with the amino acid sequence of the parent polypeptide and which retains the ability to transport a drug comprising one nucleobase moiety through the cell membrane.

The one skilled in the art is able to choose the permease which will be associated with the drug or the precursor of the drug comprising one nucleobase moiety. For example, FCY2 and Fur 4 are preferably associated with 5-FC.

Suicide gene refers to a gene coding a protein able to convert a precursor of a drug comprising one nucleobase moiety into a drug comprising one nucleobase moiety.

Suicide genes comprised but are not limited to genes coding protein having a cytosine deaminase activity, a thymidine kinase activity, an uracil phosphoribosyl transferase activity, a purine nucleoside phosphorylase activity and/or a thymidylate kinase activity.

Preferably, the suicide gene comprised in the kit of parts according to the invention codes a proteinable to transform the precursor of the drug comprising one nucleobase moiety comprised in the same kit of parts. Examples of Suicide genes and corresponding precursors of a drug comprising one nucleobase moiety are disclosed in the following table:

| Suicide gene | precursor of a drug comprising one nucleobase moiety |
|---|---|
| Thymidine Kinase | Ganciclovir; Ganciclovir elaidic acid ester; penciclovir; Acyclovir; Valacyclovir; (E)-5-(2-bromovinyl)-2'-deoxyuridine; zidovudine; 2'-Exo-methanocarbathymidine |
| Cytosine deaminase | 5-Fluorocytosine |
| Purine nucleoside phosphorylase | 6-Methylpurine deoxyriboside; Fludarabine |
| uracil phosphoribosyl transferase | 5-Fluorocytosine; 5-Fluorouracil |
| thymidylate kinase. | Azidothymidine |

According to a preferred embodiment of the invention, the suicide gene according to the invention codes a protein having at least a CDase activity. CDase is involved in the pyrimidine metabolic pathway by which exogenous cytosine is transformed into uracil by means of a hydrolytic deamination. While CDase activities have been demonstrated in prokaryotes and lower eukaryotes (Jund and Lacroute, 1970, J. Bacteriol. 102, 607-615; Beck et al., 1972, J. Bacteriol. 110, 219-228; De Haan et al., 1972, Antonie van Leeuwenhoek 38, 257-263; Hoeprich et al., 1974, J. Inf. Dis. 130, 112-118; Esders and Lynn, 1985, J. Biol. Chem. 260, 3915-3922), they are not present in mammals (Koechlin et al., 1966, Biochem Pharmacol. 15, 435-446; Polak et al., 1976, Chemotherapy 22, 137-153). The *Saccharomyces cerevisiae* (*S. cerevisiae*) FCY1 and the *E. coli* codA genes, which respectively encode the CDase of these two organisms, are known and their sequences have been published (EP 402 108; Erbs et al., 1997, Curr. Genet. 31, 1-6; WO93/01281).

CDase also deaminates an analogue of cytosine, i.e. 5-fluorocytosine (5-FC), thereby forming 5-fluorouracil (5-FU), which is a compound which is highly cytotoxic when it is converted into 5-fluoro-UMP (5-FUMP). Cells which lack CDase activity, either because of a mutation which inactivates the gene encoding the enzyme or because they are naturally deficient in this enzyme, as are mammalian cells, are resistant to 5-FC (Jund and Lacroute, 1970, J. Bacteriol, 102, 607-615; Kilstrup et al., 1989, J. Bacteriol. 1989 171, 2124-2127). By contrast, mammalian cells into which the sequences encoding CDase activity were transferred became sensitive to 5-FC (Huber et al., 1993, Cancer Res. 53, 4619-4626; Mullen et al., 1992, Proc. Natl. Acad. Sci. USA 89, 33-37; WO 93/01281). In addition, the neighboring, untransformed cells also become sensitive to 5-FC (Huber et al., 1994, Proc. Natl. Acad. Sci. USA 91, 8302-8306). This phenomenon, which is termed a bystander effect, is due to the cells which are expressing the CDase activity secreting 5-FU, which then intoxicates the neighboring cells by straightforward diffusion across the plasma membrane. This property of 5-FU in diffusing passively represents an advantage as compared with the tk/GCV reference system, where the bystander effect requires there to be contact with the cells which are expressing tk (Mesnil et al., 1996, Proc. Natl. Acad. Sci. USA 93, 1831-1835). All the advantages which CDase offers within the context of gene therapy, in particular anticancer gene therapy, can therefore be readily understood.

With this respect, according to a more preferred embodiment of the invention, the gene coding a protein having a CDase activity is FCY1 or CodA or an analogue thereof. Analogues of these genes refers to a gene having an nucleic acid sequence which have at least a degree of identity greater than 70%, advantageously greater than 80%, preferably greater than 90%, and most preferably greater than 95% with the nucleic acid sequence of the parent gene Patent application FR2004/001657 discloses a gene coding a protein having an improved CDase activity. This polypeptide derives from a native CDase by addition of an amino acid sequence. According to another preferred embodiment of the invention, the protein having a CDase activity is a polypeptide disclosed in FR2004/001657 and more preferably the polypeptide represented in the sequence identifier SEQ ID NO:1 of FR2004/001657.

In prokaryotes and lower eukaryotes, uracil is transformed into UMP by the action of uracil phosphoribosyl transferase (UPRTase). This enzyme converts 5-FU into 5-FUMP. According to another preferred embodiment the suicide gene according to the invention code a protein having an UPRTase activity.

The UPRTase in question in the present invention may be of any origin, in particular of prokaryotic, fungal or yeast origin. By way of illustration, the nucleic acid sequences encoding the UPRTases from *E. coli* (Anderson et al., 1992, Eur. J. Biochem 204, 51-56), from *Lactococcus lactis* (Martinussen and Hammer, 1994, J. Bacteriol. 176, 6457-6463), from *Mycobacterium bovis* (Kim et al., 1997, Biochem Mol. Biol. Int 41, 1117-1124) and from *Bacillus subtilis* (Martinussen et al., 1995, J. Bacteriol. 177, 271-274) may be used in the context of the invention. However, it is most particularly preferred to use a yeast UPRTase and in particular that encoded by the *S. cerevisiae* FUR1 gene whose sequence disclosed in Kern et al. (1990, Gene 88, 149-157) is introduced here by way of reference. As a guide, the sequences of the genes and those of the corresponding UPRTases may be found in the literature and the specialist databanks (SWIS-SPROT, EMBL, Genbank, Medline and the like).

Moreover, application PCT/FR99/00904 describes an FUR1 gene lacking 105 nucleotides in 5' of the coding part allowing the synthesis of a UPRTase from which the 35 first residues have been deleted at the N-terminal position and starting with the methionine at position 36 in the native protein. The product of expression of the mutant gene, designated FUR1Δ105, is capable of complementing an fur1 mutant of *S. cerevisiae*. In addition, the truncated mutant exhibits a higher UPRTase activity than that of the native enzyme. Thus, according to a particularly advantageous embodiment, the polypeptide encoded by the suicide gene according to the invention is a deletion mutant of a native UPRTase. The deletion is preferably located in the N-terminal region of the original UPRTase. It may be complete (affecting all the residues of said N-terminal region) or partial (affecting one or more continuous or discontinuous residues in the primary structure). In general, a polypeptide consists of N-terminal, central and C-terminal parts, each representing about a third of the molecule. For example, since the *S. cerevisiae* UPRTase has 251 amino acids, its N-terminal part consists of the first 83 residues starting with the so-called initiator methionine situated at the first position of the native form. As for the *E. coli* UPRTase, its N-terminal part covers positions 1 to 69.

A preferred protein having an UPRTase activity comprises an amino acid sequence substantially as represented in the sequence identifier SEQ ID NO: 1 of PCT/FR99/00904, starting with the Met residue at position 1 and ending with the Val residue at position 216. The term "substantially" refers to a degree of identity with said sequence SEQ ID NO: 1 of PCT/FR99/00904 greater than 70%, advantageously greater than 80%, preferably greater than 90%, and most preferably greater than 95%. More preferably still, it comprises the amino acid sequence represented in the sequence identifier SEQ ID NO: 1 of PCT/FR99/00904. As mentioned above, it may comprise additional mutations. There may be mentioned in particular the substitution of the serine residue at position 2 (position 37 in the native UPRTase) by an alanine residue.

According to another preferred embodiment, the suicide gene of the invention codes a protein having at least one Cdase and one UPRTase activity. Patent applications WO96/16183 and PCT/FR99/00904 describe the use of a fusion protein encoding an enzyme with two domains having the CDase and UPRTase activities and demonstrate that the transfer of a hybrid gene codA::upp or FCY1::FUR1 or FCY1::FUR1Δ105 carried by an expression plasmid increases the sensitivity of the transfected B16 cells to 5-FC. The protein and nucleic sequences described in these two applications are incorporated into the description of the present application.

Although the fusion can take place at any site of the first polypeptide, the N- or C-terminal ends are preferred and in particular the N-terminal end. Advantageously, the fusion in phase uses a second polypeptide having a cytosine deaminase (CDase) activity and which is derived from a native cytosine deaminase, such that the fusion polypeptide according to the invention exhibits the CDase and UPRTase activities. An FCY1::FUR1 fusion is preferred. Such a bifunctional polypeptide makes it possible to improve the sensitivity of the target cells to 5-FC and to 5-FU.

A CDase of prokaryotic or lower eukaryotic origin is used. More preferably still, it is a yeast CDase, and in particular that encoded by the *Saccharomyces cerevisiae* FCY1 gene. The cloning and the sequencing of the genes encoding CDases from various sources are available in the literature and specialist databanks. It should be mentioned that the sequence of the FCY1 gene is disclosed in Erbs et al. (1997, Curr. Genet. 31, 1-6). It is of course possible to use a mutant of CDase having a conversion capacity which is comparable to or greater than that of the native enzyme.

Persons skilled in the art are capable of cloning the CDase or UPRTase sequences from the published data and of carrying out possible mutations, of testing the enzymatic activity of the mutant forms in an acellular or cellular system according to the prior art technology or based on the protocol indicated in application PCT/FR99/00904, and of fusing, in particular in phase, the polypeptides with CDase and UPRTase activity, and consequently all or part of the corresponding genes.

According to a more preferred embodiment of the invention, the suicide gene codes a polypeptide comprising an amino acid sequence substantially as represented in the sequence identifier SEQ ID NO: 2 of PCT/FR99/00904, starting with the Met residue at position 1 and ending with the Val residue at position 373. The term "substantially" has the definition given above. A polypeptide comprising the amino acid sequence as represented in the sequence identifier SEQ ID NO: 2 of PCT/FR99/00904 is most particularly suitable for carrying out the invention.

Another preferred encoded polypeptide is disclosed in WO96/16183 and more preferably the polypeptide encoded by coda::upp or FCY1::FUR1.

The nucleic acid sequences may be easily obtained by cloning, by PCR or by chemical synthesis according to the conventional techniques in use. They may be native genes or genes derived from the latter by mutation, deletion, substitution and/or addition of one or more nucleotides. Moreover, their sequences are widely described in the literature which can be consulted by persons skilled in the art.

The present invention also relates to a kit of parts as presented above, characterized in that said nucleic acid sequences are inserted into one or more recombinant vectors of plasmid or viral origin, and to such recombinant vectors carrying such nucleotide sequences placed under the control of the elements necessary for their expression in a host cell.

More particularly, the kit of parts of the invention may comprise said nucleic acid sequence comprising a gene coding a permease and said nucleic acid sequence comprising a suicide gene inserted into the same recombinant vector or into distinct recombinant vectors. According to a preferred embodiment, the nucleic acid sequences are comprised into the same recombinant vector.

The present invention also relates to a recombinant vector which carries at least one of the nucleotide acid sequences according to the invention which is placed under the control of the elements which are required for expressing it in a host cell. More particularly, the present invention relates to a recombinant vector comprising a nucleic acid sequence coding a permease.

The recombinant vector can be of plasmid or viral origin and can, where appropriate, be combined with one or more substances which improve the transfectional efficiency and/or stability of the vector. These substances are widely documented in the literature which is available to the skilled person (see, for example, Feigner et al., 1987, Proc. West. Pharmacol. Soc. 32, 115-121; Hodgson and Solaiman, 1996, Nature Biotechnology 14, 339-342; Remy et al., 1994, Bioconjugate Chemistry, 5, 647-654). By way of non-limiting illustration, the substances can be polymers, lipids, in particular cationic lipids, liposomes, nuclear proteins or neutral lipids. These substances can be used alone or in combination. A combination which can be envisaged is that of a recombinant plasmid vector which is combined with cationic lipids (DOGS, DC-CHOL, spermine-chol, spermidine-chol, etc.), lysophospholipides (for example Hexadecylphosphocholine) and neutral lipids (DOPE).

According to a preferred embodiment, the cationic lipids which can be used in the present invention are the cationic lipids describes in EP901463B1 and more preferably pcTG90.

The choice of the plasmids which can be used within the context of the present invention is immense. They can be cloning vectors and/or expression vectors. In a general manner, they are known to the skilled person and, while a number of them are available commercially, it is also possible to construct them or to modify them using the techniques of genetic manipulation. Examples which may be mentioned are the plasmids which are derived from pBR322 (Gibco BRL), pUC (Gibco BRL), pBluescript (Stratagene), pREP4, pCEP4 (Invitrogene) or p Poly (Lathe et al., 1987, Gene 57, 193-201). Preferably, a plasmid which is used in the context of the present invention contains an origin of replication which ensures that replication is initiated in a producer cell and/or a host cell (for example, the ColE1 origin will be chosen for a plasmid which is intended to be produced in *E. coli* and the oriP/EBNA1 system will be chosen if it desired that the plasmid should be self-replicating in a mammalian host cell, Lupton and Levine, 1985, Mol. Cell. Biol. 5, 2533-2542; Yates et al., Nature 313, 812-815). The plasmid can additionally comprise a selection gene which enables the transfected cells to be selected or identified (complementation of an auxotrophic mutation, gene encoding resistance to an antibiotic, etc.). Naturally, the plasmid can contain additional elements which improve its maintenance and/or its stability in a given cell (cer sequence, which promotes maintenance of a plasmid in monomeric form (Summers and Sherrat, 1984, Cell 36, 1097-1103, sequences for integration into the cell genome).

With regard to a viral vector, it is possible to envisage a vector which is derived from a poxvirus (vaccinia virus, in particular MVA, canarypoxvirus, etc.), from an adenovirus, from a retrovirus, from a herpesvirus, from an alphavirus, from a foamy virus or from an adenovirus-associated virus. It is possible to use replication competent or replication deficient viral vectors. Preference will be given to using a vector which does not integrate. In this respect, adenoviral vectors and MVA are very particularly suitable for implementing the present invention.

According to a preferred embodiment, the viral vector according to the invention derives from a Modified Vaccinia Virus Ankara (MVA). MVA vectors and methods to produce such vectors are fully described in European patents EP83286 and EP206920, as well as in Mayr et al. (1975, Infection 3, 6-14) and Sutter et Moss (1992, Proc. Natl. Acad. Sci. USA 89, 10847-10851). According to a more preferred embodiment, the nucleotide sequence according to the invention may be inserted in deletion I, II, III, IV, V and VI of the MVA vector and even more preferably in deletion III (Meyer et al., 1991, J. Gen. Virol. 72, 1031-1038; Sufter et al., 1994, Vaccine 12, 1032-1040).

Retroviruses have the property of infecting, and in most cases integrating into, dividing cells and in this regard are particularly appropriate for use in relation to cancer. A recombinant retrovirus according to the invention generally contains the LTR sequences, an encapsidation region and the nucleotide sequence according to the invention, which is placed under the control of the retroviral LTR or of an internal promoter such as those described below. The recombinant retrovirus can be derived from a retrovirus of any origin (murine, primate, feline, human, etc.) and in particular from the M0MuLV (Moloney murine leukemia virus), MVS (Murine sarcoma virus) or Friend murine retrovirus (Fb29). It is propagated in an encapsidation cell line which is able to supply in trans the viral polypeptides gag, pol and/or env which are required for constituting a viral particle. Such cell lines are described in the literature (PA317, Psi CRIP GP+Am-12 etc.). The retroviral vector according to the invention can contain modifications, in particular in the LTRs (replacement of the promoter region with a eukaryotic promoter) or the encapsidation region (replacement with a heterologous encapsidation region, for example the VL3O type) (see French applications 94 08300 and 97 05203)

Preference will be also given to using an adenoviral vector which lacks all or part of at least one region which is essential for replication and which is selected from the E1, E2, E4 and L1-L5 regions in order to avoid the vector being propagated within the host organism or the environment. A deletion of the E1 region is preferred. However, it can be combined with (an)other modification(s)-/deletion(s) affecting, in particular, all or part of the E2, E4 and/or L1-L5 regions, to the extent that the defective essential functions are complemented in trans by means of a complementing cell line and/or a helper virus. In this respect, it is possible to use second-generation vectors of the state of the art (see, for example, international applications WO-A-94/28152 and WO-A-97/04119). By way of illustration, deletion of the major part of the E1 region and of the E4 transcription unit is very particularly advantageous. For the purpose of increasing the cloning capacities, the adenoviral vector can additionally lack all or part of the nonessential E3 region. According to another alternative, it is possible to make use of a minimal adenoviral vector which retains the sequences which are essential for encapsidation, namely the 5' and 3' ITRs (Inverted Terminal Repeat), and the encapsidation region. The various adenoviral vectors, and the techniques for preparing them, are known (see, for example, Graham and Prevect, 1991, in Methods in Molecular Biology, Vol 7, p 109-128; Ed: E. J. Murey, The Human Press mc).

Furthermore, the origin of the adenoviral vector according to the invention can vary both from the point of view of the species and from the point of view of the serotype. The vector can be derived from the genome of an adenovirus of human or animal (canine, avian, bovine, murine, ovine, porcine, simian, etc.) origin or from a hybrid which comprises adenoviral genome fragments of at least two different origins. More particular mention may be made of the CAV-1 or CAV-2 adenoviruses of canine origin, of the DAV adenovirus of avian origin or of the Bad type 3 adenovirus of bovine origin (Zakharchuk et al., Arch. Virol., 1993, 128: 171-176; Spibey and Cavanagh, J. Gen. Virol. 1989, 70: 165-172; Jouvenne et al., Gene, 1987, 60: 21-28; Mittal et al., J. Gen. Virol., 1995, 76: 93-102). However, preference will be given to an adenoviral vector of human origin which is preferably derived from a serotype C— adenovirus, in particular a type 2 or 5 serotype C adenovirus.

The term "replication-competent" as used herein refers to a viral vector capable of replicating in a host cell in the absence of any trans-complementation. In the context of the present invention, this term also encompasses replication-selective or conditionally-replicative adenoviral vectors which are engineered to replicate better or selectively in cancer or hyperproliferative host cells.

According to a preferred embodiment of the invention, the replication competent vector is a replication competent adenoviral vector. These replication competent adenoviral vectors are well known by the one skilled in the art. Among these, adenoviral vectors deleted in the E1b region coding the 55 kD P53 inhibitor, as in the ONYX-015 virus (Bischoff et al, 1996; Heise et al., 2000; WO 94/18992), are particularly preferred. Accordingly, this virus can be used to selectively infect and kill p53-deficient neoplastic cells. A person of ordinary skill in the art can also mutate and disrupt the p53 inhibitor gene in adenovirus 5 or other viruses according to established techniques. Adenoviral vectors deleted in the E1A Rb binding region can also be used in the present invention. For example, Delta24 virus which is a mutant adenovirus carrying a 24 base pair deletion in the E1A region (Fueyo et al., 2000). Delta24 has a deletion in the Rb binding region and does not bind to Rb. Therefore, replication of the mutant virus is inhibited by Rb in a normal cell. However, if Rb is inactivated and the cell becomes neoplastic, Delta24 is no longer inhibited. Instead, the mutant virus replicates efficiently and lyses the Rb-deficient cell.

An adenoviral vector according to the present invention can be generated in vitro in *Escherichia coli* (*E. coli*) by ligation or homologous recombination (see, for example, international application WO-A-96/17070) or else by recombination in a complementing cell line.

The elements required for expression consist of all the elements which enable the nucleotide sequence to be transcribed into RNA and the mRNA to be translated into polypeptide. These elements comprise, in particular, a promoter which may be regulable or constitutive. Naturally, the promoter is suited to the chosen vector and the host cell. Examples which may be mentioned are the eukaryotic promoters of the PGK (phosphoglycerate kinase), MT (metallothionein; Mcivor et al., 1987, Mol. Cell. Biol. 7, 838-848), α-1 antitrypsin, CFTR, surfactant, immunoglobulin, β-actin (Tabin et al., 1982, Mol. Cell. Biol. 2, 426-436) and SRa (Takebe et al., 1988, Mol. Cell. Biol. 8, 466-472) genes, the early promoter of the SV40 virus (Simian virus), the LTR of RSV (Rous sarcoma virus), the HSV-1 TK promoter, the early promoter of the CMV virus (Cytomegalovirus)., the p7.5K pH5R, pK1L, p28 and p11 promoters of the vaccinia virus, and the E1A and MLP adenoviral promoters. The promoter can also be a promoter which stimulates expression in a tumor or cancer cell. Particular mention may be made of the promoters of the MUC-I gene, which is overexpressed in breast and prostate cancers (Chen et al., 1995, J. Clin. Invest. 96, 2775-2782), of the CEA (standing for carcinoma embryonic antigen) gene, which is overexpressed in colon cancers (Schrewe et al., 1990, Mol. Cell. Biol. 10, 2738-2748) of the tyrosinase gene, which is overexpressed in melanomas (Vile et al., 1993, Cancer Res. 53, 3860-3864), of the ERBB-2 gene, which is overexpressed in breast and pancreatic cancers (Harris et al., 1994, Gene Therapy 1, 170-175) and of the α-fetoprotein gene, which is overexpressed in liver cancers (Kanai et al., 1997, Cancer Res. 57, 461-465). The cytomegalovirus (CMV) early promoter is very particularly preferred.

However, when a vector deriving from a Vaccinia Virus (as for example an MVA vector) is used, the promoter of the thymidine kinase 7.5K gene is particularly preferred.

The necessary elements can furthermore include additional elements which improve the expression of the nucleotide sequence according to the invention or its maintenance in the host cell. Intron sequences, secretion signal sequences, nuclear localization sequences, internal sites for the reinitiation of translation of IRES type, transcription termination poly A sequences, tripartite leaders and origins of replication may in particular be mentioned. These elements are known to the skilled person.

The recombinant vector according to the invention can also comprise one or more additional genes of interest, with it being possible for these genes to be placed under the control of the same regulatory elements (polycistronic cassette) or of independent elements. Genes which may in particular be mentioned are the genes encoding interleukins IL-2, IL-4, IL-7, IL-10 and IL-12, interferons, tumor necrosis factor (TNF), colony stimulating factors (CSF), in particular GM-CSF, and factors acting on angiogenesis (for example PAI-1, standing for plasminogen activator inhibitor). In one particular embodiment, the recombinant vector according to the invention comprises the gene of interest encoding IL-2 or encoding interferon γ (INFγ). It is also possible to envisage combining the nucleotide sequence according to the invention with other suicide genes such as the HSV-1 TK gene, the ricin gene, the cholera toxin gene, etc.

The present invention also relates to a viral particle which comprises a recombinant vector according to the invention. Such a viral particle can be generated from a viral vector using any technique which is conventional in the field of the art. The viral particle is propagated in a complementing cell which is suited to the deficiencies of the vector. With regard to an adenoviral vector, use will, for example, be made of the 293 cell line, which was established using human embryonic kidney cells and which efficiently complements the E1 function (Graham et al., 1977, J. Gen. Virol. 36, 59-72), of the A549-E1 cell line (Imler et al., 1996, Gene Therapy 3, 75-84) or of a cell line which permits double complementation (Yeh et al., 1996, J. Virol. 70, 559-565; Krougliak and Graham, 1995, Human Gene Therapy 6, 1575-1586; Wang et al., 1995 Gene Therapy 2, 775-783; international application WO 97/04119). It is also possible to employ helper viruses to at least partially complement the defective functions. A complementing cell is understood as being a cell which is able to supply in trans the early and/or late factors which are required for encapsidating the viral genome in a viral capsid in order to generate a viral particle which contains the recombinant vector. Said cell may not be able to complement all the defective functions of the vector on its own and, in this case, can be transfected/transduced with a vector/helper virus which supplies the additional functions.

The invention also relates to a process for preparing a viral particle, in which process:

(i) a recombinant vector according to the invention is introduced into a complementing cell which is able to complement said vector in trans, so as to obtain a transfected complementing cell, (ii) said transfected complementing cell is cultured under conditions which are appropriate for enabling said viral particle to be produced, and (iii) said viral particle is recovered from the cell culture.

While the viral particle can of course be recovered from the culture supernatant, it can also be recovered from the cells. One of the commonly employed methods consists in lysing the cells by means of consecutive freezing/thawing cycles in order to collect the virions in the lysis supernatant. The virions can then be amplified and purified using the techniques of the art (chromatographic method, method of ultra-centrifugation, in particular through a cesium chloride gradient, etc.).

The present invention, also relates to a composition which comprises a kit of parts, a recombinant vector or a viral particle according to the invention in combination with a pharmaceutically acceptable excipient A kit of parts according to the invention is more specifically intended for the preventive or curative treatment of diseases by means of gene therapy and is more specifically aimed at proliferative diseases (cancers, tumors, restenosis, etc.) and at diseases of infectious origin, in particular of viral origin (induced by hepatitis B or C viruses, HIV, herpes, retroviruses, etc.).

A kit of parts according to the invention can be made conventionally with a view to administering it locally, parenterally or by the digestive route. In particular, a therapeutically effective quantity of the therapeutic or prophylactic agent is combined with a pharmaceutically acceptable excipient. It is possible to envisage a large number of routes of administration. Examples which may be mentioned are the intragastric, subcutaneous, intracardiac, intramuscular, intravenous,= intraperitoneal, intratumor, intranasal, intrapulmonary and intratracheal routes. In the case of these three latter embodiments, it is advantageous for administration to take place by means of an aerosol or by means of instillation. The administration can take place as a single dose or as a dose which is repeated on one or more occasions after a particular time interval. The appropriate route of administration and dosage vary depending on a variety of parameters, for example the individual, the disease to be treated or the gene(s) of interest to be transferred. The preparations based on viral particles according to the invention can be formulated in the form of doses of between $10^4$ and $10^{14}$ pfu (plaque-forming units), advantageously $10^5$ and $10^{13}$ pfu, preferably $10^6$ and $10^{12}$ pfu, more preferably $10^9$ and $10^{10}$ when adenoviral particles are used and $10^6$ and $10^7$ when MVA particles are used. As far as the recombinant vector according to the invention is concerned, it is possible to envisage doses comprising from 0.01 to 100 mg of DNA, preferably from 0.05 to 10 mg, very particularly preferably from 0.5 to 5 mg.

The formulation can also include a diluent, an adjuvant or an excipient which is acceptable from the pharmaceutical point of view, as well as solubilizing, stabilizing and preserving agents. In the case of an injectable administration, preference is given to a formulation in an aqueous, non-aqueous or isotonic solution. It can be presented as a single dose or as a multidose, in liquid or dry (powder, lyophilizate, etc.) form which can be reconstituted at the time of use using an appropriate diluent. The formulation can also comprise appropriate quantities of prodrugs.

The present invention also relates to the therapeutic or prophylactic use of a kit of parts, of a recombinant vector or of a viral particle according to the invention for preparing a medicament which is intended for treating the human or animal body by gene therapy. According to a first possibility, the medicament can be administered directly in vivo (for example by intravenous injection, into an accessible tumor, into the lungs by means of an aerosol, into the vascular system using an appropriate catheter, etc.). It is also possible to adopt the ex vivo approach, which consists in removing cells from the patient (bone marrow stem cells, peripheral blood lymphocytes, muscle cells, etc.), transfecting or infecting them in vitro in accordance with the techniques of the art and then readministering them to the patient. A preferred use consists in treating or preventing cancers, tumors and diseases which result, from unwanted cell proliferation. Conceivable applications which may be mentioned are cancers of the breast, of the uterus (in particular those induced by papilloma viruses), of the prostate, of the lung, of the bladder, of the liver, of the colon, of the pancreas, of the stomach, of the esophagus, of the larynx, of the central nervous system (e.g. glioblastoma) and of the blood (lymphomas, leukemia, etc.). It can also be used in the context of cardiovascular diseases, for example in order to inhibit or retard the proliferation of the smooth muscle cells of the blood vessel wall (restenosis). Finally, in the case of infectious diseases, it is possible to conceive of the medicament being applied to AIDS.

The invention also extends to a method for treating diseases by gene therapy, characterized in that a kit of parts, a recombinant vector, a viral particle or a host cell according to the invention is administered to an host organism or cell which is in need of such treatment.

The drug comprising one nucleobase moiety or a precursor thereof can be administered in accordance with standard practice (e.g. per os, systematically). By way of illustration, regarding 5-FU, it is possible to use a dose of from 50 to 500 mg/kg/day, with a dose of 200 mg/kg/day being preferred. Within the context of the present invention, the prodrug is administered in accordance with standard practice (e.g. per os, systematically), with the administration taking place prior to, concomitantly with or else subsequent to the administration of a nucleic acid sequence according to the invention. The oral route is preferred. It is possible to administer a single dose of prodrug or doses which are repeated for a time which is sufficiently long to enable the toxic metabolite to be produced within the host organism or cell.

Furthermore, the kit of parts or method according to the invention can be combined with one or more substances which potentiate the cytotoxic effect of the drug comprising one nucleobase moiety. Mention may in particular be made of drugs which inhibit the enzymes of the pathway for the de novo biosynthesis of the pyrimidines (for example those mentioned below), drugs such as Leucovorin (Waxman et al., 1982, Eur. J. Cancer Clin. Oncol. 18, 685-692), which, in the presence of the product of the metabolism of 5-FU (5-FdUMP), increases the inhibition of thymidylate synthase, resulting in a decrease in the pool of dTMP, which is required for replication, and finally drugs such as methotrexate (Cadman et al., 1979, Science 250, 1135-1137) which, by inhibiting dihydrofolate reductase and increasing the pool of PRPP (phosphoribosylpyrophosphate), brings about an increase in the incorporation of 5-FU into the cellular RNA.

The kit of parts or method according to the invention can be combined with one or more substances effective in anticancer therapy. The kit of parts or methods according to the invention can also be use in combination with a radiotherapy.

BRIEF DESCRIPTION OF DRAWINGS

FIG. 1(A-C) illustrates antitumor activity of the combination of adenovirus and 5-FC at 125 and 50 mg/kg/day on the growth of LoVo colon cancer xenograft in Swiss nude mice.

FIG. 1 Antitumor activity of the combination of adenovirus and 5-FC at 125 and 50 mg/kg/day on the growth of LoVo colon cancer xenograft in Swiss nude mice. Tumors were established by s.c. implantation of $5 \times 10^6$ cells into nude mice. When the tumors were palpable, the animals were intratumorally inoculated 3 times with Ad-empty (A) Ad-FCU1 (B) and Ad-FCY2FCU1 (C), and treated for 3 weeks with per os administrations of 5-FC. Using Ad-empty (A), no differences in growth curves between absence and presence of 5-FC ($P>0.05$). Using Ad-FCU1 (B), there is a significant difference in the growth curves between presence and absence of 5-FC only at 125 mg/kg/day ($P<0.05$). Using Ad-FCY2FCU1 (C), there is a significant difference in the growth curves between without 5-FC and systemic 5-FC at 125 and 50 mg/kg/day ($P<0.05$).

EXAMPLES

Construction of an Adenovirus Expressing FCY2 from the E1 Region

Complete yeast purine-cytosine permease gene (FCY2, 1599 bp) was amplified from the plasmid pAJ14 (Bloch et al. 1992) as template using polymerase chain reaction (PCR). Oligonucleotides SEQ ID No 3: 5'-TAACGATCTCGAGC-CATGGTGGAAGAGGGAAATAATGTTTACG-3' (OTG14626, corresponding to the 5' end of the FCY2 coding sequence but introducing a Kozak consensus sequence replacing Leu in position 2 by a Val and incorporating an XhoI restriction site upstream of the start codon) and SEQ ID No 4: 5'-CCCTAATCACGCGTTCCTAACGAC-CGAAGTATTTTMT-3' (OTG 14627, corresponding to the 3' end and inserting a MluI restriction site downstream of the stop codon) were used as primers. The PCR product was digested by XhoI and MluI and subcloned into the corresponding sites of the mammalian expression vector pClneo (Promega) generating the plasmid pTG15829. Sequences from pTG15829 revealed a silent mutation at nucleotide +1272 (G to A) in the open reading frame of FCY2 gene. From plasmid pTG15829, the XhoI-MluI fragment containing the FCY2 gene was inserted into the transfer vector pTG13387 cleaved by the same enzymes, generating the transfer vector pTG15857. The adenoviral vector Ad-FCY2 (pTG15895) was generated by homologous recombination in the BJ5183 *E. coli* strain between the fragment PacI-BstEII of pTG15857 and the vector pTG6624 linearized by C/al. Final construction Ad-FCY2 (pTG15895) contains a deletion in E3 (nucleotides 28592 to 30470), whereas the E1 region (nucleotides 459 to 3510) was replaced by the expression cassette containing, from 5' to 3', the CMV immediate-early enhancer/promoter, a chimeric human β-globin/IgG intron, the FCY2 gene, and the bGH polyadenylation signal. The adenoviral particles expressing FCY2 (AdTG15895) were generated by transfection in a cell line complementing the E1 function (for example line PERC6).

Construction of an Adenovirus Expressing a Bicistronic Unit FCY2 IRES FCU1 from the E1 Region:

The NheI-NotI fragment of the plasmid pTG15829 containing the FCY2 gene was isolated and introduced into the vector pTG14347 (plasmid pTG4369p53FCU1 described in p53FCU1 patent) linearized with NheI-NotI. The plasmid pTG16055 thus obtained contains, from 5' to 3', the FCY2 gene, the IRES (Internal Ribosome Entry Site) sequence of ECMV (encephalomyocarditis virus), and the FCU1 gene. From plasmid pTG16055, the NheI-BamHI fragment was inserted into the transfer vector pTG14799 (plasmid described in FCU1-8 patent) cleaved by the same enzymes, generating the transfer vector pTG16066. The adenoviral vector Ad-FCY2FCU1 (pTG16079) was generated by homologous recombination in the BJ5183 E. coli strain between the fragment PacI-BstEII of pTG 16066 and the vector pTG6624 linearized by ClaI. Final construction Ad-FCY2FCU1 (pTG16079) contains a deletion in E3 (nucleotides 28592 to 30470), whereas the E1 region (nucleotides 459 to 3510) was replaced by the expression cassette containing, from 5' to 3', the CMV immediate-early enhancer/promoter, a chimeric human β-globin/IgG intron, the FCY2 IRES FCU1 bicistronic unit, and the bGH polyadenylation signal. The adenoviral particles expressing FCY2 IRES FCU1 (AdTG16079) were generated by transfection in a cell line complementing the E1 function (for example line PERC6).

5-Fluorocytosine Uptake Assays:

The human tumoral cell line A549 (ATCC CCL-185) was infected with Mock, an empty adenovirus (AdTG15149), an adenovirus expressing FCU1 (AdTG14800 described in FCU1-8 patent) or FCY2 (AdTG15895) or FCY2 and FCU1 (AdTG16079). The cells ($5.10^6$) were infected at MOI 20 and plated on 60-mm plates. After 24 hours, uptake of 5-FC into transfected cells was measured by conventional tracer techniques. The initial rate of 5-FC (10 µM, room temperature) was measured using a 1-min incubation period and was traced with [$^3$H]5-FC at a concentration of 0.15 µCi/ml.

Briefly, 24 hours after infection, cells were washed once with the transport buffer (100 mM NaCl, 2 mM KCl, 1 mM $CaCl_2$, 1 mM $MgCl_2$ and 10 mM HEPES, pH 7.5). Uptake assays were started by adding 2 ml of transport buffer containing 5-FC at 10 µM ([$^3$H]5-FC at 0.15 µCi/ml). At the end of the incubation, extracellular label was removed by three rapid washes with ice-cold transport buffer. The cells were solubilized in 1 ml of 5% SDS for quantification of radioactivity by liquid scintillation counting.

TABLE 1

Uptake of 5-FC into transfected A549 cells:

| Vector | Uptake of 5-FC (pmol/min/5 · $10^6$ cells) |
|---|---|
| Mock | 7.97 ± 3.76 |
| Ad-empty (AdTG15149) | 9.74 ± 3.31 |
| Ad-FCU1 (AdTG14800) | 13.28 ± 5.74 |
| Ad-FCY2 (AdTG15895) | 38.94 ± 7.61 |
| Ad-FCY2FCU1 (AdTG16079) | 77 ± 28.7 |

Uptake of 5-FC was measured using transport buffer containing 10 µM of 5-FC.
Each values represents the average of three independent experiments ± SD.

The results presented in Table I demonstrate an increase in 5-FC transport in cells infected by Adenoviruses expressing FCY2 (AdFCY2 and AdFCY2FCU1). Such results indicate that the yeast FCY2, expressed in human cells, encodes a functional 5-FC transporter.

In Vitro Cell Sensitivity to 5-FC:

Tumor cells infected with the different adenoviruses were compared for their sensitivity toward 5-FC. The human tumor cell line A549 (ATCC CCL-185) was infected with Mock, an empty adenovirus (AdTG15149), an adenovirus expressing FCU1 (AdTG14800 described in FCU1-8 patent) or FCY2 (AdTG15895) or FCY2 and FCU1 (AdTG16079). The cells were infected at an MOI of 1 and then cultured in the presence of different concentrations of 5-FC. After 6 days of culture, the viability of the cells was determined using trypan blue. The $LD_{50}$ values for 5-FC listed in Table 2 are the means of four counts.

In Vivo Experiments:

The objective of this study is to compare the antitumor activity of the recombinant Ad-FCU1 and Ad-FCY2FCU1 in combination with per os administration of 5-fluorocytosine (5-FC) at 125 or 50 mg/kg/day in nude mice bearing LoVo human colon tumors.

LoVo cells were injected subcutaneously (s.c.) into the flanks of Swiss nude mice. Each animal was implanted with $5 \times 106$ LoVo cells suspended in 100 ml of PBS. When tumors had reached 30-50 mm3, the mice were randomized in a blinded manner and treated with the indicated vectors at dose of 1.108IU. The vectors (suspended in 100 ml of 10 mM Tris-HCl, pH7.5, 1 mM $MgCl_2$) were directly injected into the tumor at days 12, 15 and 18 after tumor implantation. From day 12 on, 5-FC was given by oral gavage at 62.5 mg/kg/day (0.6 ml 5-FC 0.25% in water) or at 25 mg/kg/day (0.6 ml 5-FC 0.1% in water) twice a day during 3 weeks. Tumor size was measured in two dimensions using calipers. Tumor volume were calculated in mm3 using the formula (p 6)(length×width2).

Statistical analyses were performed using the non-parametric Mann-Whitney U test and Statistica 6.1 software (StatSoft, Inc.). A P<0.05 was considered to be statistically significant.

Figure 1:
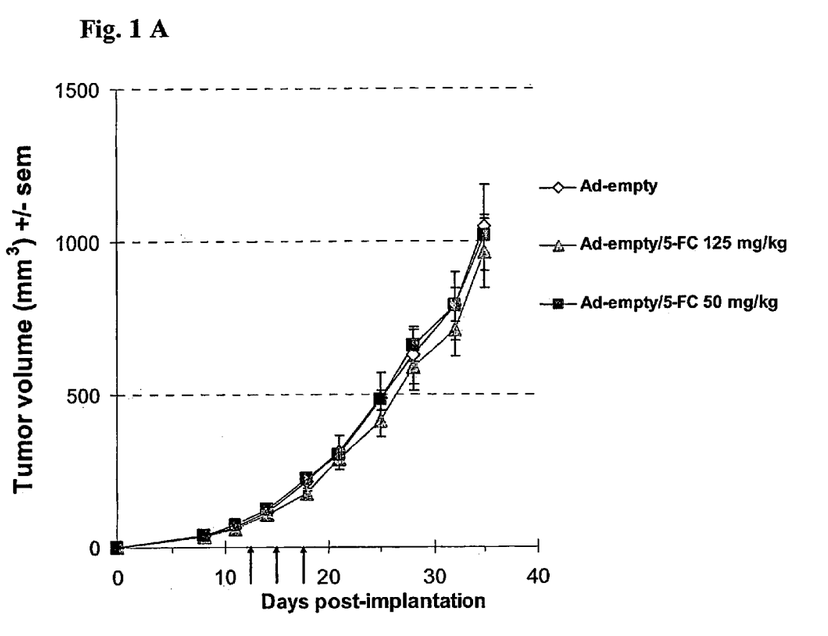

Using administration of 5 FC at 125 mg/kg/day, injection of Ad-FCU1 and Ad-FCY2FCU1 resulted in a statistically significant suppression of tumor growth (FIGS. 1B,C). This antitumor effect was specific of FCU1/5-FC because infection Ad-empty, which does not induce FCU1 activity, did not significantly reduce tumor size in presence of 5-FC (FIG. 1A). At a lower dose of 5-FC (50 mg/kg/day), a significant inhibition of tumor growth was observed after delivery of Ad-FCY2FCU1 (FIG. 1C), whereas no modification in tumor growth was observed using Ad-FCU1. This result indicates that the combination of FCY2 and FCU1 is significantly more effective than FCU1 alone and suggests that the FCY2FCU1/5-FC system is more efficient than the FCU1/5-FC system in a cancer gene therapy approach.

TABLE 2

$LD_{50}$ values for 5-FC of adenovirus-transduced A549 cells:

| Vector | $LD_{50}$ (µM) |
|---|---|
| Mock | >1000 |
| Ad-empty (AdTG15149) | >1000 |
| Ad-FCU1 (AdTG14800) | 50 |
| Ad-FCY2 (AdTG15895) | >1000 |
| Ad-FCY2FCU1 (AdTG16079) | 20 |

These results demonstrate that coexpression of the FCY2 and FCU1 genes from adenoviral vector (AdTG16079) sensitizes the cells to 5-FC more strongly than does the expression of the FCU1 gene (AdTG14800). This greater sensitivity to 5-FC results from the uptake of 5-FC encoded by the FCY2 gene. Using cells infected with Ad-FCY2 (AdTG15895), no antiproliferative effect was observed, this indicates that the sole administration of FCY2, in absence of cytosine deaminase activity, is insufficient for an effective antitumor therapy protocol.

The invention claimed is:

1. A recombinant vector comprising a gene coding a permease and a suicide gene, wherein
the gene coding a permease is the gene coding the S. cerevisiae permease FCY2; and
the suicide gene codes a fusion protein having a cytosine deaminase activity and an uracil phosphoribosyl transferase activity, said suicide gene comprising a first nucleic acid sequence coding FUR1Δ105 and a second nucleic acid sequence coding FCY1.

2. The recombinant vector according to claim 1, wherein said vector is selected from the group consisting of plasmid and viral vectors.

3. The recombinant vector according to claim 2, wherein said recombinant vector is combined with one or more substances which improve(s) the transfectional efficacy or the stability, or both, of the vector.

4. The recombinant vector according to claim 3, wherein said substance which improve the transfectional efficacy or the stability, or both, of the vector is selected from the group consisting of cationic lipids, cationic polymers, lysophospholipides and polypeptides.

5. The recombinant vector according to claim 2, wherein said vector is a viral vector which is obtained from a pox virus, from an adenovirus, from a retrovirus, from a herpes virus, from an alphavirus, from a foamyvirus or from an adenovirus associated virus.

6. The recombinant vector according to claim 5, wherein said vector is obtained from a Modified Vaccinia Ankara (MVA) virus.

7. The recombinant vector according to claim 6, wherein said gene coding a permease and said suicide gene are inserted at a site of a naturally occurring deletion within the MVA genome selected from the group consisting of deletion I, II, III, IV, V and VI.

8. The recombinant vector according to claim 7, wherein said genes are inserted in the site of the naturally occurring deletion III.

9. The recombinant vector according to claim 5, wherein said vector is an adenoviral vector which additionally lacks all or part of the non-essential E3 region.

10. A pharmaceutical composition comprising a recombinant vector comprising a gene coding a permease and a suicide gene, wherein
the gene coding a permease is the gene coding the S. cerevisiae permease FCY2; and
the suicide gene codes a fusion protein having a cytosine deaminase activity and an uracil phosphoribosyl transferase activity, said suicide gene comprising a first nucleic acid sequence coding FUR1Δ105 and a second nucleic acid sequence coding FCY1.

11. The pharmaceutical composition according to claim 10, wherein said vector is selected from the group consisting of plasmid and viral vectors.

12. The pharmaceutical composition according to claim 11, wherein said vector is a viral vector which is obtained from a pox virus, from an adenovirus, from a retrovirus, from a herpes virus, from an alphavirus, from a foamyvirus or from an adenovirus associated virus.

13. The pharmaceutical composition according to claim 12, wherein said vector is obtained from a Modified Vaccinia Ankara (MVA) virus.

14. The pharmaceutical composition according to claim 13, wherein said gene coding a permease and said suicide gene are inserted at a site of a naturally occurring deletion within the MVA genome selected from the group consisting of deletion I, II, III, IV, V and VI.

15. The pharmaceutical composition according to claim 14, wherein said genes are inserted in the site of the naturally occurring deletion III.

16. The pharmaceutical composition according to claim 15, wherein said vector is an adenoviral vector which additionally lacks all or part of the non-essential E3 region.

17. The pharmaceutical composition according to claim 10, further comprising one or more substances which improve(s) the transfectional efficacy or the stability, or both, of the vector.

18. The pharmaceutical composition according to claim 17, wherein said one or more substances are selected from the group consisting of cationic lipids, cationic polymers, lysophospholipides and polypeptides.

* * * * *